United States Patent
Lashmore et al.

[11] Patent Number: 6,042,781
[45] Date of Patent: *Mar. 28, 2000

[54] AMBIENT TEMPERATURE METHOD FOR INCREASING THE GREEN STRENGTH OF PARTS

[75] Inventors: David S. Lashmore, Lebanon; Glenn L. Beane, Hanover; Lev Deresh, West Lebanon, all of N.H.

[73] Assignee: Materials Innovation, Inc., West Lebanon, N.H.

[*] Notice: This patent is subject to a terminal disclaimer.

[21] Appl. No.: 08/762,864

[22] Filed: Dec. 10, 1996

Related U.S. Application Data

[63] Continuation-in-part of application No. 08/317,729, Oct. 4, 1994, which is a continuation-in-part of application No. 08/133,316, Oct. 8, 1993, abandoned, which is a continuation-in-part of application No. 07/802,420, Dec. 4, 1991, Pat. No. 5,318,746.

[51] Int. Cl.[7] ............................................ B22F 1/04
[52] U.S. Cl. ........................ 419/62; 419/64; 419/66
[58] Field of Search ................... 419/30, 34, 35, 419/36, 40, 62, 64, 66

[56] References Cited

U.S. PATENT DOCUMENTS

| | | |
|---|---|---|
| Re. 29,093 | 12/1976 | Burns . |
| 2,040,179 | 5/1936 | Livingston et al. . |
| 3,004,332 | 10/1961 | Werner . |
| 3,466,203 | 9/1969 | Tarr et al. . |
| 3,704,508 | 12/1972 | Di Giambattista . |
| 3,859,086 | 1/1975 | Church et al. . |
| 3,914,507 | 10/1975 | Fustukian . |
| 3,933,961 | 1/1976 | Burns . |
| 4,181,757 | 1/1980 | Youdelis . |
| 4,218,507 | 8/1980 | Deffeves et al. . |
| 4,235,631 | 11/1980 | Aliotta et al. . |
| 4,323,395 | 4/1982 | Li . |
| 4,426,404 | 1/1984 | Shoher et al. . |
| 4,427,501 | 1/1984 | Rogers . |
| 4,450,188 | 5/1984 | Kawasumi . |
| 4,528,207 | 7/1985 | Johnson . |
| 4,664,855 | 5/1987 | Tremblay et al. . |
| 4,742,861 | 5/1988 | Shoher et al. . |
| 4,859,412 | 8/1989 | Groll et al. . |
| 4,963,184 | 10/1990 | Diehl et al. . |
| 4,970,050 | 11/1990 | Groll et al. . |
| 4,990,394 | 2/1991 | Shoher et al. . |
| 4,997,699 | 3/1991 | Shoher et al. . |
| 5,026,519 | 6/1991 | Peralta ........................ 419/30 |
| 5,064,690 | 11/1991 | Sando et al. . |
| 5,112,572 | 5/1992 | Eerkes et al. ................ 419/30 |
| 5,118,317 | 6/1992 | Wijnen . |
| 5,183,631 | 2/1993 | Kugimiya et al. . |
| 5,268,233 | 12/1993 | Heller et al. .............. 428/523 |
| 5,276,290 | 1/1994 | Bladon . |
| 5,302,464 | 4/1994 | Nomura et al. . |
| 5,334,240 | 8/1994 | Ferrier . |
| 5,344,605 | 9/1994 | Kaji et al. . |
| 5,384,087 | 1/1995 | Scorey . |
| 5,711,866 | 1/1998 | Lashmore et al. . |

FOREIGN PATENT DOCUMENTS

| | | |
|---|---|---|
| 0 291944 | 11/1988 | European Pat. Off. . |
| 2 216 545 | 10/1989 | United Kingdom . |

OTHER PUBLICATIONS

Goetzel, C.G., "Treatise on Powder Metallurgy" pp. 248–250 (1949) vol. 1, Technology of Metal Powders and Their Products.

Greener, et al., "Dental Amalgams", Dental Materials: Properties and Selection, Quintessence Publishing Co. Inc. (1989) pp. 263–281.

Masuhura, et al., Study on Toxicity of a New Gallium Alloy for Dental Restorations, Journal of Dental Health, 27 p. 361, (1987).

Ishii, et al., "The Primary Irritant Testing to mthe Human Skin of Gallium Alloy", J. Fukuola Dent. College, 14(1) : 96–112 (1987) p. 49.

Horibe, et al., "Gallium Alloys for Dental Restoration", J. Fukuoka Dent. College, 12 (4) :198–204 (1986) p. 33.

Jouyiama, H., et al., "Studies on Biological Evaluation of Gallium Alloy", J. Fukuoka Dent. Coll., 14(3) :249–257 (1987) p. 40.

Kim et al., "The Clinical Observation of Gallium Alloy as a New Dental Restorative Material for Primary Teeth", J. Fukuoka Dent. Coll., 14(4) :395–400 (1988) p. 56.

S. R. Natarajan,et al., "Electroplating Baths for Silver—A Review of Cyanide–Free Formulations", Metal Finishing, Feb. 1971, p. 51–56.

Fackelma, "Can Dental Fillings Create Drug Resistance", Science News, Apr. 1993.

*Primary Examiner*—Ngoclan Mai
*Attorney, Agent, or Firm*—Fran S. Wasserman

[57] ABSTRACT

A process for consolidating powder, particulates, foils or sheets of metal coated composites, elemental metallic or metallic alloy or intermetallic compounds into net shapes having increased green strength at or near ambient temperature comprises treating the material with an aqueous activation solution. The aqueous activation solution is selected from dilute acids, reducing agents, molten salt electrolytes and mixtures thereof. Pressure is used to consolidate the treated powders, particulates, foils or sheets into a net shape at or near ambient temperature.

32 Claims, 4 Drawing Sheets

AMBIENT TEMPERATURE METHOD FOR INCREASING THE GREEN STRENGTH OF PARTS

This application is a continuation-in-part of U.S. patent application Ser. No. 08/317,729, filed Oct. 4, 1994, (hereby incorporated by reference herein in its entirety) which in turn is a continuation-in-part of U.S. patent application No. Ser. No. 08/133,316, filed Oct. 8, 1993, now abandoned, which is in turn a continuation-in-part of U.S. patent application Ser. No. 07/802,420, filed Dec. 4, 1991, which issued on Jun. 7, 1994 as U.S. Pat. No. 5,318,746.

FIELD OF INVENTION

The invention relates to methods for consolidating powders, particulates, continuous fibers, foils or sheets of metal, metal alloys, metal coated materials and intermetallic materials to make net shape or near net shape articles. More specifically, this invention relates to methods and activation solutions for consolidating these materials at ambient temperatures to make parts or articles having an increased green strength and a net or near net shape. In use, the method and activation solutions can be used to consolidate materials for any number of applications, including, dental restorations, high temperature materials, materials for thermal management, alloys for shape memory effect applications, high strength alloys, composites, semiconductor alloys (TiSnNi), and in technology used for coating and printing parts.

BACKGROUND OF THE INVENTION

In powder metallurgy, very small diameter (<1 μm to 200 μm) powder particles are charged into the die cavity of die presses and then compressed into parts or shapes. After initial compression these parts are typically less than 100% dense and the powder particles are much less than 100% bonded together. In many instances the relative number of "welded" points between particles is very low, producing a part that is considerably fragile. The strength of such a part is commonly called the "green" strength and is typically 50% or less than the strength of a 100% well bonded part. In order to obtain a fully bonded, in many instances denser part, this green formed part is then sintered at high temperature. In many cases a lubricant is added to the powder before pressing. In this circumstance, the lubricant has to be removed by a "delubing": burn off at a temperature below the sintering temperature. Typically, the temperatures used for sintering are at an appreciable fraction of the melting point (Tm) of the compressed metals or alloys, usually above 0.8 Tm. Sintering collapses the internal porosity of the green part and eventually results in a dense but usually less than a 100% well bonded part. The part is however, distorted in shape from the green part as pressed, mostly due to changes in density, and in some cases due to phase changes that may occur during sintering. Thus, present powder metallurgy methods are limited in that they cannot be used to produce parts having complex geometries and those that are made from materials that undergo undesirable phase changes at the high sintering temperatures necessary for bonding particle to particle.

For some active alloy powders which tend to oxidize readily in air, such as aluminum and titanium alloys, powder metallurgy (i.e., handling, consolidating and/or pressing) must be done with great care to avoid explosion. In Japan, aluminum powder metallurgy has been banned for this reason.

This explosion hazard is due to the extreme tendency of bare aluminum powder to oxidize and the usual air formed oxide prevents aluminum from cold-welding to itself. Water atomized aluminum has an even thicker surface oxide and consequently this oxide is incorporated into the structures of parts into which the aluminum powder may be used. Its presence degrades the thermal characteristics and other properties of the aluminum part. Hence, high temperature sintering is required to promote bonding of aluminum particles to each other.

When metal foils or sheets are used as starting materials, consolidation is often done by hot roll bonding. The hot rolling breaks up the naturally occurring oxide on the surface of the material, thereby enabling the surfaces of the powder particles (foils or sheets) to weld together at a sufficient number of contact points so as to provide adequate adhesion between the individual particles, sheets or foils. An example of such a hot roll bonding process can be found in U.S. Pat. No. 5,384,087 to Scorey. Such processes are not always satisfactory because they result in final structures having oxides incorporated therein. The significant amount of deformation required to break up these oxides can cause high internal stress which in turn require annealing and result in shape distortion.

In certain technologies parts or coatings are "printed" onto a substrate when, liquid metals, ceramics or mixtures are heated to extreme temperatures and projected onto a substrate with sufficient velocity to cause the material to weld to itself and to the substrate upon impact. Such processes are however limited, since they do not allow for precise control over the deposition process and hence cannot be used to produce printed parts which require great precision such as those used in micro-electronics and micro-imaging. These processes further allow oxides and porosity to be incorporated into the final deposited part. Additionally, since the temperature limits of apparatuses used to project the materials onto the substrates do not go high enough to permit the liquefaction of a number of materials, as for example copper, the type of materials that can be deposited using thermal spray technologies and hence the final product is limited.

SUMMARY OF THE INVENTION

It is therefore an object of the present invention to provide a safe process for consolidating to net shape or near net shape at ambient temperature (cold welding) or using dramatically reduced sintering temperature (0.5 Tm or less) some types of otherwise hazardous powder, particulate, foil or sheet materials into parts which have greater than typical bonding between particles or green strength as pressed. The present invention provides a process whereby net shaped or near net shaped parts that are well bonded are formed at ambient or low temperatures. Parts formed in accordance with the present invention do not need to be high temperature sintered to achieve final strength or density. The inventive process can be applied to any process by which parts or articles are made by consolidating powders, particulates, foils or sheets of materials. These include traditional powder metallurgy wherein powders or particulates are consolidated in the die cavity of a powder press and thermal and non-thermal spray technologies wherein materials are projected at high velocity to consolidate them upon impact onto a substrate.

The present invention process also increases the safety of powder metallurgy by constraining the powders under an aqueous solution eliminating air borne particulates around compacting machinery. Moreover, in one embodiment of the invention when powders, such as aluminum are coated with a less reactive metal, such as copper, the aluminum powder is made less explosive due to slower oxidation in air. Another example is titanium coated with nickel. Because the contact area of the coating to the particle is increased, an additional objective of the present invention is to provide an approach to low temperature compound formation in large quantities, using a method which takes advantage of the interdiffusion processes occurring at relatively low temperatures and ambient pressure. The metal powders can be compacted at ambient temperature, below the melting points of the surface treated powders present in the mixture, under pressure sufficient to form a uniform metallic composite, and subsequently reacted at relatively low temperatures (at $T \leq 0.5$ Tm) to form the desired intermetallic compound.

DETAILED DESCRIPTION OF PREFERRED EMBODIMENTS

Figure 1:
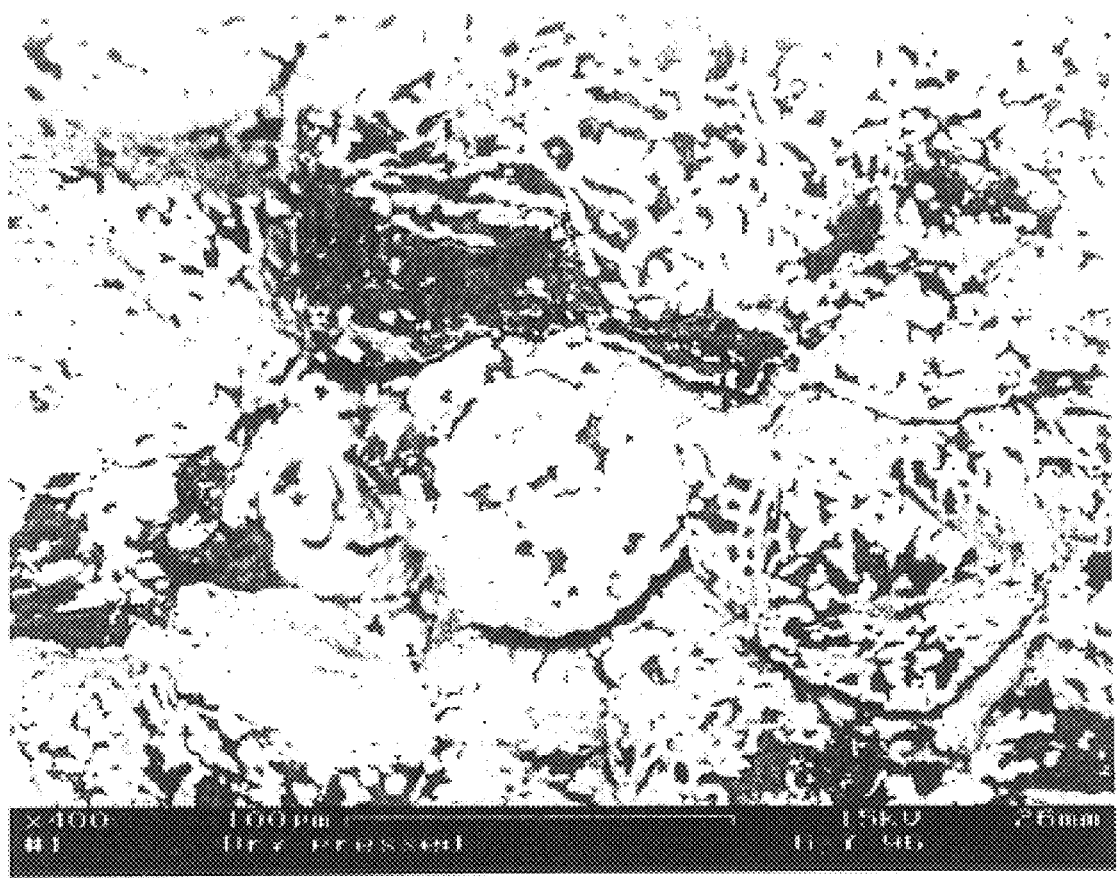
FIG. 1 is a scanning electron micrograph showing the fracture surface of green copper aluminum.

The present inventors have found that, as an alternative to traditional high temperature sintering, cold-welding and net shape part or article formation from powders, particulates, foils and sheets of materials can occur at ambient temperature. Using the inventive process, the "green strength" of the consolidated materials is increased when cold welding takes place across particle surfaces that are in contact with each other when the particles are appropriately treated with the activation solutions of the present invention. In one embodiment, the present invention is directed to an ambient temperature process that increases the green strength of an article or part to the point where high temperature sintering is not needed for producing a net shape, fully dense article or part in a powder press. In another embodiment, the present inventive process can be used to coat parts or print parts using ambient temperature materials projected onto a substrate using high velocity but without the need for heat to liquefy the materials.

For purposes of this invention, "net shape" is intended to mean the final or net shape, size and density at which a part or article is intended to be used. The net shape, size and density of the article or part will not deviate substantially from the net shape after any subsequent processing steps. Exceptions to this are alloys undergoing a phase change when sintering such as titanium aluminum, aluminum nickel, or titanium nickel tin. For example, in processes for making parts or articles by consolidating particulates and subsequently strengthening the part by high temperature sintering, the shape of the part or article after, not before, the sintering step would be its net shape. High temperature sintering alters the shape, size and density of the consolidated article. For purposes of this invention, at ambient temperature is intended to mean without adding a considerable external heat source (enough to effect the density (internal porosity) of the part or article) to the process. For purposes of this invention, "fully dense" is intended to mean that density at which a part or article would have been after high temperature sintering in a process for producing such an article requiring a high temperature sintering step. The same exception as noted above concerning alloys that undergo phase changes does however, apply here also.

The present inventive process can be used to produce a net shape or near net shape article having increased green strength from powders, particulates (i.e., wires, whiskers, fibers), foils or sheets of materials. For purposes of this invention, "increased green strength" is intended to mean a green strength that is greater than that which would be obtained by consolidating the material under some type of pressure. Alternatively, the process, when used in conjunction with technologies to project materials onto a substrate that are used to print parts (e.g., circuit boards, engraving plates, etc.) or coat parts by impacting powdered materials together and onto a substrate. The process comprises treating the powder, particulate, foil or sheet material with an aqueous activation solution and using pressure to consolidate the treated material into a net or near net shape at or near ambient temperature. In many instances, no further processing steps, in particular high temperature sintering, the application of an external source of considerable heat or machining to net shape is needed to produce a fully dense, well bonded, net shape part or article. Further, using the present process, dissimilar materials such as silicon carbide, tungsten or graphite can be bonded to aluminum (copper coated aluminum) by coating each of the respective materials with a metal such as copper and using the present activation solutions and pressure to bond them together. This bonding has heretofore only been possible using processes that distort part shapes or require an adhesive.

In the inventive process, the step of treating the material can take place in situ, as for example in the die cavity of a powder metallurgy press or in a separate container whereby the slurry of material and activation solution that results from the treating step can then be transferred to a die cavity in a powder press. An example of such a container is the feed shoe (powder delivery system) of a powder press. Alternatively, in instances where the present invention is used to coat items, make or print parts by using sufficient velocity to project the material onto a substrate, the container can be the receptacle of an apparatus appropriate for doing so.

Materials that can appropriately be consolidated to form net shape parts by employing the present inventive process include, but are not limited to, metal, metal alloys, intermetallic compounds and combinations thereof. Other materials like ceramics, composites (mixtures of materials not reactive with each other that behave according to rule of mixtures) and any metal or alloy that are very negative with respect to the hydrogen electrode potential can be consolidated to net shape parts by coating them with a layer of metals, alloys or intermetallics otherwise appropriate for use in this invention. For example, such metals include, but should not be construed to be limited to all metals having a standard potential greater than hydrogen such as platinum, palladium, silver, gold, rhodium, rhenium, germanium, antimony, ruthenium, osmium, copper, iridium, antimony and arsenic. Additionally, metals having a standard potential slightly less than but close to hydrogen such as iron, nickel, cobalt, tin and indium may be appropriate materials for directly consolidating (or projecting) to make parts or articles or for coating onto other materials that might not otherwise consolidate using the present process. Metal alloys appropriate for the cold welding process of the present invention (and as coatings for other materials) include, but are not limited to alloys of iron (e.g. steel), alloys of copper (e.g., brass, bronze), and lead alloys (e.g., solder).

Exemplary materials that can be coated with an appropriate metal or alloy and then consolidated to a net shape or near net shape part by the present invention, include powders, particulates, sheets or foils of stainless steel, zinc, iron, titanium, hafnium, molybdenum, tantalum, niobium, vanadium, zinc, gallium, lanthanum, rhenium, tin, yttrium, scandium, thorium, cerium, praseodymium, neodynium, samorium, gadolinium, terbium, holmium, erbium, thulium, ytterbium, lutetium, graphite, diamond, tungsten, aluminum, silicon carbide, tungsten carbide, molybdenum, titanium, nickel, and iron. As demonstrated by the foregoing list, certain materials such as nickel can be consolidated coated or uncoated or can itself be used as a coating. All of the aforementioned materials can be initially provided with the respective coating of a metal such as nickel, cobalt, or copper or alternatively, the present invention can comprise the optional step of coating the respective material to be consolidated prior to treating it with the activation solution.

The appropriate metal coating should in general, be readily deformable. As mentioned briefly above, particularly preferable coating materials are metals that have respective standard potentials greater than hydrogen (0 volts with respect to the hydrogen electrode (VSHE)). This coating step can be carried out using any known method of coating particulates, foils or sheets such as electrochemical deposition, CVD, PVD or ball milling.

Amongst those materials that can initially be provided to the process with a coating are those materials that have been coated to engineer the property of the material (obtain a part or article that has at least one property that is not the same as the coating nor the core material). In these, the coating may be relatively thick and can range from about 10% to about 50% by weight of the coated material. The actual thickness will vary depending on the particular size of the particles and is governed by the engineered propert(ies) of the final materials that one wishes to obtain. When materials are coated for the purpose of allowing the materials to be consolidated using the activation solutions of the present invention, the coating is usually provided to the material in an additional step to the present process and the thickness of the coating is relatively thin to minimize the appearance of the properties of the coating material in the compressed part or article. Thus the coating is intended only to act (in conjunction with the activation solution) as a "glue" for holding the materials together. In such a coating, the amount of coating is preferably from about 1% to about 10% by weight. This thickness will of course vary with the specific material being used. In both instances, however, the thickness of the coating should be sufficient to uniformly coat substantially the entire surface of the material to be treated and consolidated.

The optional coating step can be carried out using any known method of coating particulates, foils or sheets. These include coatings deposited thereon from both a gaseous or a liquid phase. Methods for depositing coatings from the gaseous phase include all such known methods. Specific examples include fluidized bed deposition, vacuum evaporation, sputtering, and plasma assisted chemical vapor deposition. Coatings from a liquidphase include but are not limited to electrolytic, as for example electrolytic coating from a fluidized bed or centrifugal bed onto particles or fibers; immersion or substitution deposition and chemical reduction. One example of a fluidized bed coating technique is described in a copending application of some of the present inventors, U.S. patent application Ser. No. 08/673,135 entitled "Electrochemical Fluidized Bed Coating of Powders", hereby incorporated herein in its entirety by reference. The material can also be coated using centrifugal bed technology, as for example that described in a copending patent application of some of the present inventors, U.S. patent application Ser. No. 08/568,637, entitled "Centrifugal Bed Coating of Powders", hereby incorporated herein in its entirety by reference.

The present inventive process can also be used to consolidate intermetallic materials as for example, $Ag_4Sn$, $Ag_3Sn$, $Ni_3Al$, $NiAl$, $TiNiSn$, $Al_2Cu$, $AlCu_2$, $Al_3Cu_2$, $Al_4Cu_9$ and $TiNi$. Some of these intermetallics find specific use in the field of dentistry as dental restorations and can be consolidated when appropriately treated with an activation solution according to the invention. Likewise, metal alloys, as for example alloys of copper, silver, cobalt and nickel can be consolidated to make or print parts at ambient temperatures using the present invention.

In the present process, the materials to be consolidated are treated with an aqueous activation solution to prepare their surfaces to cold weld to each other under pressure at ambient temperature. The aqueous activation solution should preferably be comprised of one of an acid, a reducing agent, mixtures thereof or a molten salt electrolyte. Although not wanting to be bound by any one theory, the present inventors believe that any solution capable of removing the oxide (and nitrides or contaminants) from the surface of the material to be consolidated to tie degree necessary to allow points on the material to cold weld to each other upon application of pressure and thereby increase the green strength of the resultant part or article is appropriate for use in the present invention. of course, the nature and specific concentration of each respective component of the activation solution depends on the nature of the application, i.e. the specific material being cold-welded and the specific properties required of the resultant part or article.

Any aqueous media can be used as the solvent into which the acid or reducing agent is dissolved to produce the aqueous activation solution. Suitable solvents include, but are not limited to, water, oil, methanol, toluene, benzene, nitric acid, ethanol, hydrochloric acid, hydrofluoric acid, hydrobromic acid and molten salts such as chloroaluminate and methylzolium chloride. Acidified water is preferred as the solvent for the activation solution.

Appropriate acids for use in the aqueous activation solution, include, but are not limited to, fluoboric acid, sulfuric acid, hydrofluoric acid, hydrochloric acid, citric acid, adipic acid, ascorbic acid, sodium ascorbate, potassium ascorbate, sulfamic acid, ammonium biflouride, nitric acid, acetic acid, acetoacetic acid, anisic acid, ascorbic acid, benzoic acid, hydroiodic acid, hydrobromic acid, and mixtures thereof. In all instances, the pH of the acid should preferably be equal to or near its pKa. Further, the preferred range of concentration for the acid in the aqueous solution should be from about 0.1% to about 10% by weight, at a temperature of from about 25° to about 50° C. The controlling characteristic should be the pH of the acid in the solution, hence all other parameters should be adjusted to ensure the appropriate pH of the acid in solution.

The following Table is illustrative of typical acid components of the activation solution and their respective preferred pH for use in methods and activation solutions in accordance with the present invention.

TABLE I

| Acid | Preferred pH |
|---|---|
| acetic | 4.75 |
| acetoacetic | 3.58 |
| acrylic | 4.25 |
| adipamic | 4.63 |
| adipic | 4.43 |
| m-aminobenzoic | 4.68 |
| p-aminobenzoic | 4.92 |
| o-aminobenzosulfonic | 2.48 |
| m-aminobenzosulfonic | 3.73 |
| anisic | 4.47 |
| o-β-anisylpropionic | 4.80 |
| m-β-anisylproprionic | 4.65 |
| p-β-Anislpropionic | 4.69 |
| ascorbic | 4.10 |
| D-L-Aspartic | 3.86 |
| Barbituric | 4.01 |
| Benzoic | 4.19 |
| m-bromobenzoic | 3.86 |
| α-butyric | 4.81 |
| iso-butyric | 4.84 |
| a-caproic | 4.83 |
| iso-caproic | 4.84 |

When a reducing agent is used in the aqueous activation solution of the present invention, the following non-limiting list of reducing agents at their respective preferred pHs are appropriate for use: dimethylamino borane at a pH of from about 8 to about 12, sodium borohydride at a pH of from about 1 to about 5, sodium hypophosphite at a pH of from about 3 to about 7, sodium bisulfite at a pH of from about 2 to about 6, hydrazine at a pH of from about 2 to about 6, hydroquinone at a pH of from about 2 to about 10, pyrocatechol at a pH of from about 2 to about 10, resorcinol at a pH of from about 2 to about 10, sodium sulfite at a pH of from about 1 to about 5, formaldehyde at a pH of from about 2 to about 5 and mixtures thereof. The reducing agent is preferably used in the aqueous activation solution at a concentration of from about 1% to about 10% by weight, at a temperature of from about 25° to about 50° C. In all instances, the concentration of the reducing agent should be adjusted to achieve the desired pH.

Additionally, it should be understood that oxidation couples such as $Sn^{+2}$ that can oxidize to $Sn^{+4}$, $Cu^{+1}$ that can oxidize to $Cu^{++}$ and $Co^{++}$ that can oxidize to $Co^{+++}$ may also be used as reducing agents.

Alternatively, a molten salt electrolyte can be used as the aqueous activation solution. Preferred molten salt electrolytes for use in the present process include, but are not limited to, solutions of methylzolium chloride, aminozolium chloride, amidozolium chloride, chloroaluminate and mixtures thereof. Typically the molten salt electrolyte should be present in the aqueous solution at a concentration of about 100% by weight, at a temperature of about 25° to about 300° C.

The present invention should not be construed to be limited to treating the appropriate material by applying an aqueous activation solution thereto. The surfaces on powders, particulates, sheets and foils can also be, for example, electrolytically treated in appropriate reducing solutions by applying a negative potential with respect to another electrode. In particular, iron can be treated in solutions containing sulfate by applying a negative potential thereto. This alternative treatment step is however, less desirable than treating the materials with an activation solution, since the particles will not cold weld once the potential (voltage) is removed due to many complex absorption possibilities. Other methods for removing oxides from the metal surfaces and preventing further oxide formation thereon, other than the electrochemical method described above, may also be used. Additionally, treating the powder, particulate sheet or foil material with gas plasmas of inert and reducing atmospheres, such as the forming gas (5% hydrogen and 95% nitrogen), also may be suitable for activating the surfaces prior to the step of consolidating the material.

In all instances, regardless of the active component(s) of the activation solution, the solution can further contain at least one additive. Such additives can include surfactants, reducing agents, lubricants, viscosity reducing agents, combinations of the foregoing and elements that have standard potentials less than hydrogen. Viscosity reducing agents can include alcohols such as methanol, ethanol, propanol and glycerol. A particularly preferred additive is colloidal teflon (PTFE, polytetrafluoroethylene). The inclusion of colloidal teflon (PTFE, polytetrafluoroethylene) can aid the ejection of an article or part made by the present invention when consolidated in a die press. The particles of teflon (PTFE) can additionally contain corrosion inhibitors or lubricants.

In particularly preferred embodiments, the present inventive process consolidates copper coated materials, as for example, copper coated aluminum (powders, particulates, foils or sheets) and is used in conjunction with an activation solution comprised of an aqueous solution of acetic acid at a pH of from about 1.5 to about 3 at a concentration of from about 5% by weight to about 20% by wt. at a temperature of from about 25° to about 50° C. Copper coated tungsten is preferably treated with an activation solution comprised of an aqueous solution of fluoboric acid at a pH of from about 0.1 to about 5 at a concentration of from about 0.5% by weight to about 20% by weight at a temperature of from about 25° to about 50° C. Copper coated silicon carbide and copper coated molybdenum are preferably treated similarly to copper coated tungsten.

Once treated, the powders, particulates, foils or sheets are consolidated into a net or near net shape part or article having increased green strength (increased to eliminate the need for a high temperature sintering step). Additionally, prior to consolidation, metallic and/or non-metallic hard components such as oxide, carbide or nitride particles in the form of high-strength structural whisker, particulate, fiber or wire additives can be incorporated into the mixture. Such additives may also include, but are not limited to, alumina powder, silicon carbide powder, graphite, diamond, sapphire, boron carbide, tungsten carbide or the like. Other whisker, fiber or particle additives are also within the scope of the invention.

In the present invention, the pressure used to consolidate the material of choice into a net shape part or article can be provided by any known method or machinery known to exert pressure to consolidate materials to make parts. Preferred means of consolidating the materials include, but are not limited to, manual instrumentation (as for example a hand operated uniaxial press, dental instruments, and hammers), a die press, a forging press, a coining press, an isostatic press, extrusion or roll bonding. Additionally, the pressure can be provided by the impact of particle on particle and on substrate when they are projected with sufficient velocity to cause such impact. The step of providing the pressure can take place in situ and almost simultaneously with the treatment step or appropriately treated materials can be moved to another location for pressure consolidating.

In general, any known method for consolidating materials to make parts or articles, including those methods used in producing dental restorations (handpieces, vibratory hammers) is suitable for use in the present invention. By compressing the treated, sometimes coated powder in appropriate dies, or, alternatively, by the use of processes such as extrusion forming or injection molding, the treated material can be formed into a net or near-net shape part having increased green strength.

When the step of consolidating the material takes place in the die cavity of a powder press, the preferred pressure for consolidating the material to a cohesive solid ranges from about 20 Kpsi to about 120 Kpsi. Of course, the specific pressure used will vary with the material being consolidated, the complexity and the desired density of the part or article being made or printed and the load rate of the press. Some materials are load rate sensitive, such as copper coated aluminum and ferrous alloys. In such instances, preferred loading rates (speed of die punch) should be from about 0.5 mm/second to about 100 mm/second. Commercial mechanical powder presses having load rates of about 100 mm/second are preferred.

The liquid present between the suitably treated material is forced out from between the powders, particulates, foils or sheets during the consolidation step by the pressure generated during compaction. Alternatively, the liquid can be removed prior to the actual consolidation by any appropriate means for doing so, as for example by vacuum. The liquid, in addition to enabling the particles to weld to each other provides a very important secondary benefit by constraining very small powder particles under the surface of the liquid so that they can be handled more safely. In instances where the particles are used as in situ dental restorations, the patient will not inhale them.

Another benefit of the aqueous solution is lubrication of the compressed particles in the die cavity of a powder press. If minute amounts of surfactants as for example, but not limited to DELRYN, DF-16 (polyethoxylated alcohol/ polyethylene glycol), triton x-1a (octyl phenoxypolyethoxyethanol), florade (3M,C-135 fluorochemical surfactant), sodium lauryl sulfate or colloidal material such as PTFE are added to the activation solution, when the wet powders are pressed in the die cavity the lubricant particles are pushed outward toward the die surface to act as a lubricant on that surface. Removal (ejection) of the finished part from the cavity is thus facilitated.

In embodiments where the pressure for consolidating the materials is provided by high velocity projection, powdered materials treated with activation solution should be propelled with sufficient velocity to provide the energy and momentum to cause the particles to cold weld upon impact with each other and a substrate. Typical velocities for propelling the particles should range from about 200 m/s to about 2000 m/s with the lower end of the range being preferred.

The properties of the resultant part or article are determined by the properties of the starting materials, by the relative amount of each component, by the treatment used and by the desired density of the final part or article. The density is controlled by the details of the consolidation procedure that was used. Thus, in general, increasing values of pressure applied for consolidation increase the density, and thereby the compressive strength and rupture strength of the final product.

In a further embodiment, the present invention comprises a process for consolidating powders, particulates, foils or sheets of iron or iron alloys (i.e., steel) into net or near net shapes having increased green strength at or near ambient temperature. The process comprises the steps of treating the iron or stainless steel with an aqueous activation solution comprised of a halide containing acid and using pressure to consolidate the treated iron or stainless steel into a fully dense net shape at ambient temperature.

In certain instances, it may also be desirable here to coat the iron or iron alloys with any of the aforementioned metals appropriate for coating having a standard potential greater than hydrogen or close enough to the standard potential, prior to treating it with the aqueous activation solution. Suitable coatings for this step should be selected from those set forth above and can be applied using the same coating techniques and to the same respective thickness.

Examples of suitable halide containing acids and their respective pHs, for use in the aqueous activation solution when iron or iron alloys compacted compacted to a net or near net shape article or part having an increased green strength, include, but are not limited to, HCl at a pH of from about 1 to about 3, HBr at a pH of from about 1 to about 3, HI at a pH of from about 1 to about 3, HF at a pH of from about 1 to about 3 and fluoboric acid at a pH of from about 1 to about 3. The halide containing acid is preferably present in the aqueous solution at a concentration of from about 5% to about 10% by weight, at a temperature of from about 25° to about 50° C. An additional component of this activation solution comprises reducing agents such as those already mentioned above as well as small quantities of other acids such as acetic acid to adjust pH. In this embodiment, as in others, the aqueous activation solution may also further comprise additives.

The present invention is also directed to a process for imparting the ability to consolidate to a net shape part having increased green strength under pressure at ambient temperature to a particulate non metal, metal, metal alloy or intermetallic material. The process comprises the steps of adding to the material an amount of aqueous activation solution in a concentration and at a pH sufficient to impart to the particulate material the ability to form a net shape part having increased green strength when pressure is applied thereto. The activation solution comprises an acid, a reducing agent, or mixtures thereof, as in previously described embodiments or a molten salt electrolyte. The choice of appropriate pH and concentration of the acid, reducing agent and molten salt electrolyte for this embodiment is also the same as that described in detail above for other embodiments of this invention.

This process, like those described in detail above can further comprise the step of coating the particulate with a metal having a standard potential greater than hydrogen (or close to it) prior to the step of adding the aqueous activation solution.

In this embodiment, as in others, an additional step of providing an inert atmosphere (non-oxidizing) after treating the material may be used in instances when the treating step is done in a receptacle apart both spatially and temporally from that in which the consolidation takes place. In this activation solution may be removed before transferring the particulate material into a die cavity, provided that the powders are prevented from oxidation during the transfer by providing an atmosphere of a suitable inert gas such as argon or nitrogen, or active gas such as forming gas mixtures (argon and hydrogen or nitrogen and hydrogen).

In all the aforementioned embodiments, when powders are consolidated to make or print parts or articles, the preferred powder size is preferably from about 0.1 micron to about 150 microns, more preferably from about 10 to about 50 microns and most preferably from about 15 to about 40 microns. Such powder sizes can be obtained directly from the source or alternatively the powders can be appropriately sieved to be within the desired size range.

This invention is also directed to an activation solution for producing net shaped or near net shape parts from particulate iron or iron alloys (coated or uncoated). The activation solution comprises an aqueous solution of from about 0.1 to about 20 ml/L, preferably from about 1 to about 10 ml/L of a halide containing acid, at a temperature of from about 25° to about 50° C. The halide containing acid is selected from the group consisting of HCl at a pH of from about 1 to about 3, preferably a pH of 2; HBr at a pH of from about 1 to about 3, preferably at a pH of 1–2; HI at a pH of from about 1 to about 3, preferably at a pH of from about 1 to about 2; HF at a pH of from about 1 to about 3, preferably at a pH of from about 1 to about 2; and fluoboric acid at a pH of from about 1 to about 3, preferably at a pH of from about 1 to about 2.

The aqueous activation solution in accordance with this invention may further comprise an additive. Examples of additives suitable for use in the present invention include, but are not limited to surfactants, lubricants, colloidal teflon (PTFE), reducing agents, graphite and mixtures of acids. A viscosity reducer such as for example an alcohol such methanol, ethanol, propanol or glycerol may also be included in the solution.

While the invention will now be more fully described in connection with certain preferred embodiments in the following Examples, it will be understood that it is not intended to limit the invention to these particular embodiments. On the contrary, it is intended to exemplify alternatives, modifications and equivalents as may be included within the scope of the invention as defined by the appended claims. Thus the following Examples which include preferred embodiments will serve to illustrate the practice of this invention, it being understood that the particulars described are by way of example only and for purposes of illustrating discussion of preferred embodiments of the present invention only and are presented to provide what is believed to be the most useful and most readily understood description of the procedure as well as of the principles and conceptual aspects of the invention.

EXAMPLES

Example 1
Copper Coated Aluminum

Figure 2:
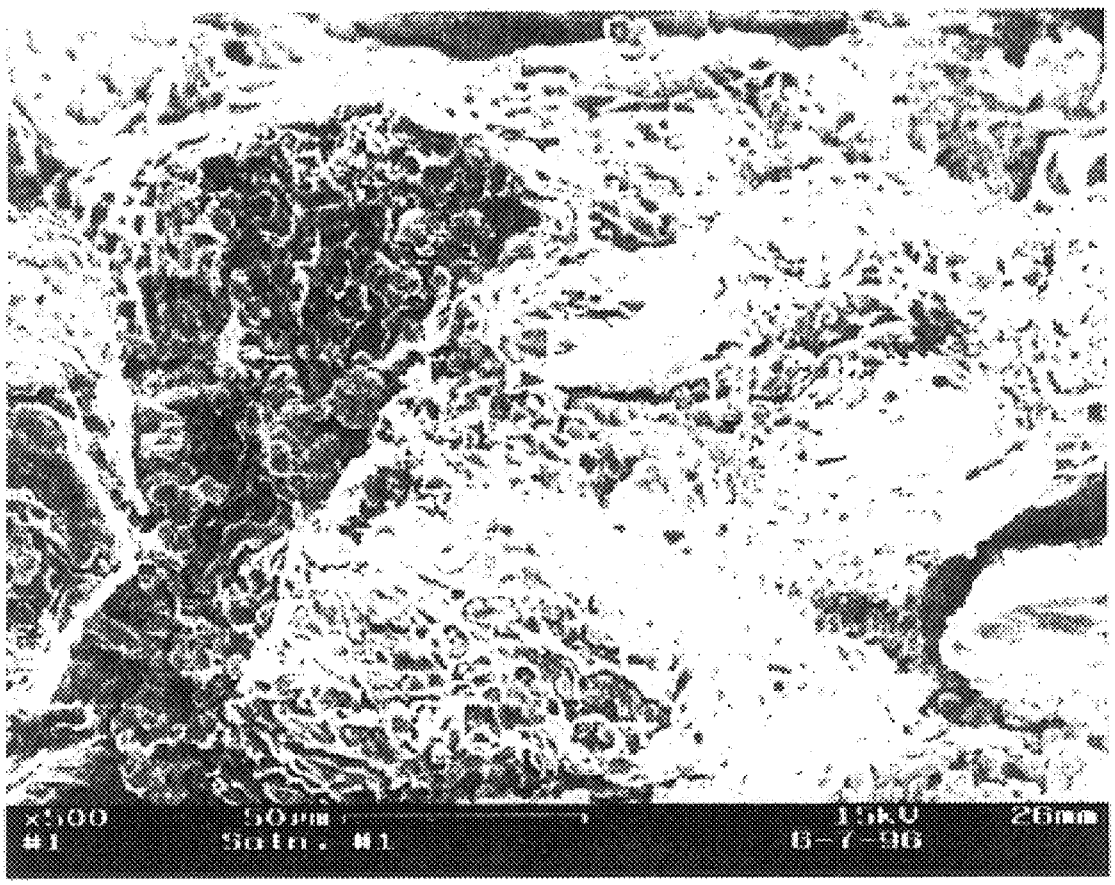
FIG. 2 is a scanning electron micrograph showing the fracture surface of copper aluminum pressed according to the method of the present invention.
Figure 4:
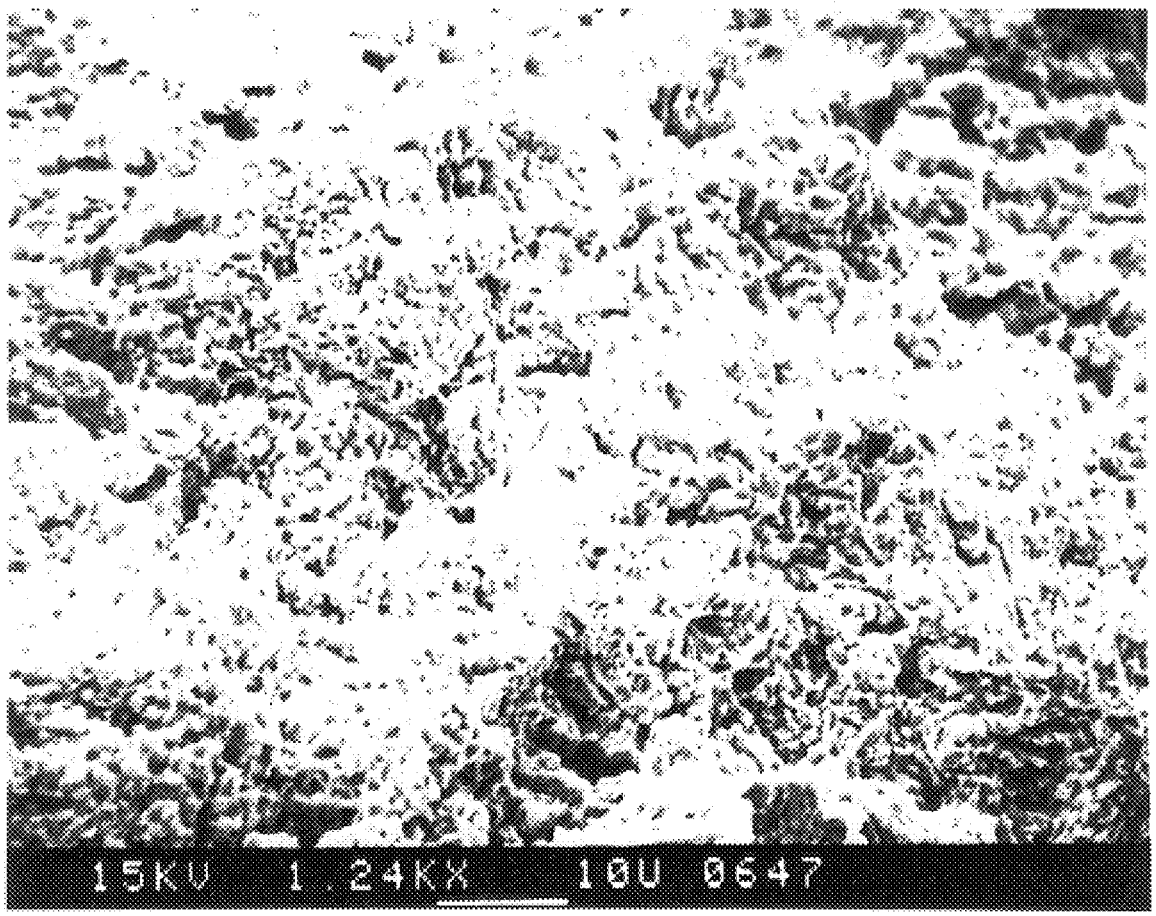
FIG. 4 is an optical micrograph of a polished cross section of copper aluminum pressed in accordance with the process of the present invention. Complete copper coverage can be observed around each grain of aluminum.

Aluminum powder 99.99% (HP601, AMPEL, Palmerton, Pa.) is coated with about 31% copper by weight in accordance with the Centrifugal Bed coating procedure taught in U.S. patent application Ser. No. 08/568,637, hereby incorporated by reference in its entirety herein. The coating process uses 99.99% oxygen free copper anodes and a pyrophosphate based electrolyte. The aluminum powder is sieved to be within particle size between 60 and 150 microns. Two grams of the sieved powder is then blended with 5–10ml of 5% acetic acid to form a slurry. The excess acid is decanted and the resultant slurry placed in a 0.5 inch mold consisting of a set of cylindrical pins and a corresponding die. The die is allowed to float and the slurry is pressed on a hand operated press (DAKE 50H) to density of 5.12 g/cc at 200 Ksi to produce SampleA. The fracture surface of this material is shown in the micrograph of FIG. 2 and a polished cross section of this material is shown in FIG. 4.

The same procedure as above is repeated without adding the acetic acid to produce Sample B. The fracture surface of sample B is shown in the micrograph of FIG. 1. Thermal conductivity and density is measured for Samples A and B and the results are in Table II below.

TABLE II

| Aluminum Coated with Copper 31% by Weight | Sample A | Sample B |
|---|---|---|
| Thermal Conductivity | 219 w/m° K. | 87 w/m° K. |
| density | 5.12 g/cc | 5.18 g/cc |

Example 2
Copper-silicon Carbide

Silicon carbide particles (Carborundum, 15 to 150 micron spherical particles) are coated with about 70% copper by weight in accordance with the centrifugal bed process referenced above. The powder is sieved to be within particle size between 15 and 20 microns and 2 grams of the sieved powder is then blended with an aqueous activation solution of 5–10 ml 5% fluoboric acid. The excess acid was decanted and the resultant slurry placed in a 0.5 inch mold and pressed on a hand operated press (DAKE 50H) to density of 7.119 g/cc at 200 Ksi to produce Sample C.

The same procedure as above was repeated without adding the activation solution to produce Sample D.

Thermal conductivity and density is measured for Samples C and D and the results are reported in Table III below.

TABLE III

| Silicon carbide coated with copper 70% by Weight. | Sample C | Sample D |
|---|---|---|
| thermal conductivity | 263 w/m° K. | 80.31 w/m° K. |
| density | 7.11 g/cc | 7.2 g/cc |

Example 3
Copper

Two grams of 99.99% copper powder (Fukuda, FCC-115A) of particle size 20 to 150 microns is blended with 5–10 ml 5% fluoboric acid. The excess acid is decanted and the resultant slurry placed in a 0.5 inch mold on a hand operated press (DAKE 50H) and pressed to density of 8.9 g/cc at 200 Ksi to produce Sample E.

Figure 3:
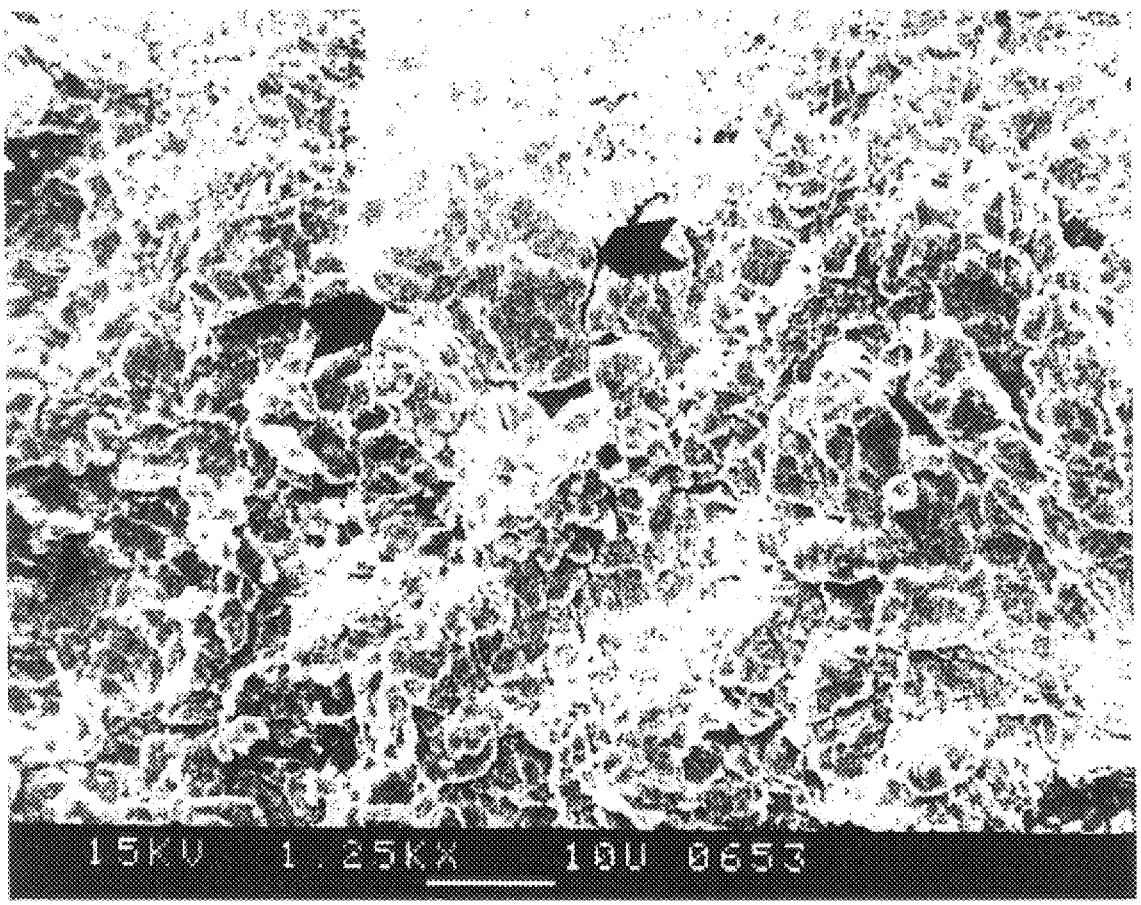
FIG. 3 is a scanning electron micrograph showing the fracture surface of copper pressed according to the method of the present invention.

FIG. 3 shows a scanning electron micrograph showing the fracture surface of this material.

The same procedure as above was repeated without adding the fluoboric acid solution to produce Sample F.

Thermal conductivity and density is measured for Samples E and F and the results are reported in Table IV below.

TABLE IV

| Copper | Sample E | Sample F |
|---|---|---|
| thermal conductivity | 395 w/m° K. | 140 w/m° K. |
| density | 8.51 g/cc | 8.42 g/cc |

Example 4
Iron

Two grams, of 99.9% iron powder (Haegonaes 1000 C) of particle size 44 microns, are blended with 5% hydrobromic acid. The excess acid is decanted and the resultant slurry placed in a 0.5 inch mold and pressed on a 50 ton hand operated press (DAKE 50H) to 100% density of 7.8 g/cc at 200 Ksi to produce Sample G.

The same procedure as above is repeated without adding the fluoboric acid solution to produce Sample H.

Example 5
Copper Coated Aluminum

Aluminum powder 99.996 (HP601, AMPEL, Palmerton, Pa.) is coated with about 31% copper by weight in accordance with the centrifugal bed coating procedure referenced above using 99.99% deoxygenated copper anodes and a pyrophosphate based electrolyte. The powder is sieved to be within particle size between 60 and 150 microns and 2 grams of this powder is than blended with an aqueous activation solution of 10 ml 100% acetic acid, 5 ml 98% sulfuric acid and 85 ml water to form a slurry. The excess acid is decanted and the resultant slurry is placed in a 0.5 inch mold consisting of a set of cylindrical pins and a corresponding die. The die is allowed to float and the slurry is pressed on a hand operated press (DAKE 50H) to 100% density of 3.964 at 200 Ksi to produce Sample I.

Thermal conductivity and density is measured for Sample I and the results are compared to those for Sample B and reported in Table V below.

TABLE V

| Copper Aluminum | Sample I | Sample B |
|---|---|---|
| thermal conductivity | 215 W/m° K. | 87 w/m° K. |
| density | 3.964 g/cc | 5.18 g/cc |

While the invention has been illustratively described herein with reference to various preferred features, aspects and embodiments, it will be appreciated that the invention is not thus limited, and may be widely varied in respect of alternative variations, modifications, and other embodiments, and therefore the invention is to be broadly construed as including such alternative variations, modifications and other embodiments within the spirit and scope of the invention claimed.

What is claimed is:

1. A process for producing a net or near net shape, article or part at or near ambient temperature from a material having a metal coating disposed thereon, said material being in the form of powders, particulates, foils or sheets, said process comprising the steps of:

treating the material having a metal coating disposed thereon, wherein the metal coating is selected from the group consisting of platinum, palladium, silver, gold, indium, tin, nickel, copper, cobalt, rhodium, rhenium, germanium, antimony, ruthenium, osmium, iridium, antimony, iron and arsenic, with an aqueous activation solution to form a slurry; and using pressure to consolidate the slurry at or near ambient temperature into a net or near net shape part or article having an increased green strength over that which it would otherwise have had when consolidated with pressure without being treated with the activation solution.

2. The process according to claim 1, optionally further comprising the step of removing the activation solution from the material either contemporaneously with or before the step of using pressure to consolidate.

3. The process according to claim 1, wherein said aqueous activation solution is comprised of an aqueous solution of one of the group consisting of an acid, a reducing agent, mixtures thereof and a molten salt electrolyte.

4. The process according to claim 1, wherein the acid is present in the solution at a pH equal to or near its pKa and is selected from the group consisting of fluoboric acid, sulfuric acid, hydrofluoric acid, hydrochloric acid, citric acid, adipic acid, ascorbic acid, sodium ascorbate, potassium ascorbate, sulfamic acid, ammonium biflouride, nitric acid, acetic acid, acetoacetic acid, anisic acid, benzoic acid, hydroiodic acid, hydrobromic acid, and mixtures thereof.

5. The process according to claim 4, wherein the acid is present in the aqueous solution at a concentration of from about 0.1% to about 20% by weight, at a temperature of from about 25° to about 50° C.

6. The process according to claim 1, wherein the coating disposed on the metal material is selected from the group consisting of platinum, palladium, silver, gold, indium, tin, nickel, copper, cobalt, rhodium, rhenium, germanium, antimony, ruthenium, osmium, iridium, antimony, iron and arsenic.

7. The process according to claim 6, wherein the material having a coating of metal disposed thereon is selected from the group consisting of copper coated graphite, copper coated diamond, copper coated tungsten, copper coated aluminum, copper coated silicon carbide, copper coated molybdenum, nickel coated titanium, cobalt coated tungsten, tin coated nickel, and tin and nickel coated titanium, copper coated iron, cobalt coated iron or steel or nickel coated iron or steel and zinc coated iron or zinc coated steel, copper coated tungsten carbide, nickel coated tungsten carbide, iron coated tungsten carbide, nickel coated graphite, iron coated graphite, silver coated graphite, copper coated permalloy (FeNi).

8. The process according to claim 7, wherein the material having a coating of metal disposed thereon is copper coated aluminum and the activation solution is acetic acid at a pH of from about 1.5 to about 3 at a concentration of from about 5 to about 20% by weight at a temperature of from about 25° to about 50° C.

9. The process according to claim 7, wherein the material having a coating of metal disposed thereon is copper coated silicon carbide and the activation solution is fluoroboric acid at a pH of from about 0.1 to about 5 at a concentration of from about 0.5 to about 20% by weight at a temperature of from about 25° to about 50° C.

10. The process according to claim 7, wherein the material having a coating of metal disposed thereon is copper coated molybdenum and the activation solution is fluoroboric acid at a pH of from about 0.1 to about 5 at a concentration of from about 0.5 to about 20% by weight at a temperature of from about 25° to about 50° C.

11. The process according to claim 1, wherein the material having a coating of metal disposed thereon is selected from the group consisting of metal coated tungsten carbide, metal coated silicon carbide and metal coated ceramic.

12. The process according to claim 1, wherein the pressure is provided by one of the group consisting of manual instrumentation, a die press, a forging press, a coining press, an isostatic press and roll bonding.

13. The process according to claim 1, wherein the pressure is provided by high velocity projection to impact powder particle upon powder particle and upon a substrate.

14. The process according to claim 1, wherein the activation solution further comprises at least one additive.

15. The process according to claim 13, wherein the additive is colloidal teflon (PTFE).

16. The process according to claim 13, wherein the additive is a viscosity reducing agent.

17. The process according to claim 1, wherein when said material has a standard potential less than hydrogen, the coating disposed on said material is a metal having a standard potential greater than hydrogen or close to that of hydrogen.

18. The process according to claim 17, wherein the metal having a standard potential greater than or close to that of hydrogen is selected from the group consisting of platinum, palladium, gold, silver, copper, nickel, tin, indium, cobalt, rhodium, ruthenium, arsenic, antimony and rhenium.

19. The process according to claim 17, wherein the coating layer is from about 50 nm to about 5000 nm thick.

20. The process according to claim 17, wherein the material having a standard potential less than hydrogen is selected from the group consisting of stainless steel, iron, titanium, hafnium, molybdenum, tantalum, niobium, vanadium, zinc, gallium, lanthanum, and tin.

21. A process for consolidating particulates, foils or sheets of iron or iron alloys into net or near net shapes at or near ambient temperature comprising the steps of:

coating the iron or iron alloy with a metal coating having a standard potential greater than or close to that of hydrogen prior to the step of treating the iron or iron alloy;

treating the iron or iron alloy with an aqueous activation solution comprised of a halide containing acid; and using pressure to consolidate the treated iron or stainless steel into a net or near net shape at ambient temperature having increased green strength over that which it would otherwise have had when consolidated with pressure without being treated with the activation solution.

22. The process according to claim 21, wherein the metal coating is selected from the group consisting of platinum, palladium, gold, silver, copper, cobalt, nickel, tin, indium, rhodium, rhenium, ruthenium, antimony, arsenic, iridium, and zinc.

23. The process according to claim 21, wherein the halide containing acid is selected from the group consisting of HCl at a pH of from about 1 to about 3, HBr at a pH of from about 1 to about 3, HI at a pH of from about 1 to about 3, HF at a pH of from about 1 to about 3 and fluoboric acid at a pH of from about 1 to about 3.

24. The process according to claim 23, wherein the halide containing acid is present in the aqueous solution at a concentration of from about 0.1% to about 20% by weight, at a temperature of from about 25° to about 50° C.

25. The process according to claim 21, wherein the iron alloy is steel and the aqueous activation solution further comprises acetic acid in an amount to adjust the pH of the solution to about 3.1.

26. A process for producing a net shape, article or part at or near ambient temperature from a copper coated material selected from the group consisting of copper coated powders, copper coated particulates, copper coated foils and copper coated sheets, said process comprising the steps of:

treating the copper coated material with an aqueous activation solution comprised of an acid at a pH at or near its pKa and selected from the group consisting of fluoboric acid, sulfuric acid, hydrofluoric acid, hydrochloric acid, citric acid, adipic acid, ascorbic acid, sodium ascorbate, potassium ascorbate, sulfamic acid, ammonium biflouride, nitric acid, acetic acid, acetoacetic acid, anisic acid, benzoic acid and mixtures thereof; and using pressure to consolidate the treated copper coated material into a net shape having increased green strength over that which is would otherwise have had when consolidated with pressure without being treated with the activation solution at or near ambient temperature.

27. The process according to claim 26, wherein the acid is present in the aqueous solution at a concentration of from about 0.1% to about 20% by weight at a temperature of from about 25° to about 50° C.

28. The process according to claim 26, wherein the acid is acetic acid at a pH of from about 1.5 to about 3 and at a concentration of from about 5 to about 20% by weight.

29. A process for imparting to a powder or particulate non metal, metal, metal alloy or intermetallic material the ability to consolidate to a net or near net shape part under pressure at ambient temperature comprising the steps of:

coating the powder or particulate with a metal having a standard potential greater than or close to hydrogen; and adding to said coated powder or particulate material an amount of aqueous activation solution comprising one of the group consisting of an acid, a reducing agent, mixtures thereof and a molten salt electrolyte in a concentration and at a pH sufficient to impart to the particulate material the ability to form a net shape or near net shape part when pressure is applied thereto.

30. The process according to claim 29, further comprising the steps of removing said solution from the treated material and providing an environment of an inert gas to the treated material to maintain said ability.

31. The process according to claim 29, wherein the acid is present in the aqueous solution at a pH equal to or near its pKa and is selected from the group consisting of fluoboric acid, sulfuric acid, hydrofluoric acid, hydrochloric acid, citric acid, adipic acid, ascorbic acid, sodium ascorbate, potassium ascorbate, sulfamic acid, ammonium biflouride, nitric acid, acetic acid, acetoacetic acid, adipic acid, anisic acid, ascorbic acid, benzoic acid and mixtures thereof.

32. The process according to claim 31, wherein the acid is present in the aqueous solution at a concentration of from about 5% to about 20% by weight, at a temperature of from about 25° to about 50° C.

* * * * *